United States Patent [19]

Peoples

[11] 4,184,082
[45] Jan. 15, 1980

[54] LINEAR FLAW DETECTOR

[75] Inventor: Patrick J. Peoples, Intervale, N.H.

[73] Assignee: Howell Laboratories, Incorporated, Bridgton, Me.

[21] Appl. No.: 947,518

[22] Filed: Oct. 2, 1978

Related U.S. Application Data

[63] Continuation of Ser. No. 810,406, Jun. 27, 1977, abandoned, which is a continuation of Ser. No. 638,290, Dec. 8, 1975, abandoned.

[51] Int. Cl.² .......................................... G01N 21/32
[52] U.S. Cl. .................................... 250/572; 356/446
[58] Field of Search ............... 250/562, 563, 571, 572; 356/364, 371, 445, 446, 447, 448

[56] References Cited

U.S. PATENT DOCUMENTS

| | | | |
|---|---|---|---|
| 3,922,093 | 11/1975 | Dandliker et al. | 250/571 |
| 3,984,189 | 10/1976 | Seki et al. | 356/446 |
| 4,029,420 | 6/1977 | Simms | 356/446 |

*Primary Examiner*—David C. Nelms
*Attorney, Agent, or Firm*—Richard L. Stevens

[57] ABSTRACT

A linear flaw detector for coated surfaces. An incident beam is provided and sensed above and below the theoretical specular angle. Where a flaw occurs, the reflected signal changes in intensity. By sensing above and below the specular angle, the signal corresponding to the flaw is accented in reference to the signals from the background. The signal corresponding to the flaw may then be separated from background noise and an output provided.

17 Claims, 4 Drawing Figures a b c d

LINEAR FLAW DETECTOR

This is a continuation of application Ser. No. 810,406, filed June 27, 1977, abandoned which is a continuation application of Ser. No. 638,290 filed Dec. 8, 1975, abandoned.

BACKGROUND OF THE INVENTION

In coating moving surfaces, such as paper webs, certain defects are produced if the coating is not applied uniformly by the coating blade. Such coating flaws or linear flaws may be produced by an obstruction in the coating nip, dilatency of the coating or coating inconsistency.

The present decection methods used are primarily the observations of the machine operators. This is totally unsatisfactory in that in the case of a paper web, it normally would move as fast as 2,000 ft. per minute and it is very difficult to detect and report coating defects. Electronic devices to detect flaws are available. One such device includes shoulder-to-shoulder silicon detectors. The detectors may or may not scan a predetemined portion of the width of the web. The sensing elements of such detectors generally provide an incident beam such as from a light emmitting diode and the reflected beam is collected by a photocell. When the beam of light traverses a gloss variation, the reflected signal is greatly reduced. The photocell senses this light level change at the specular angle, automatically compensating for gloss variations, and an output signal is provided.

In coating paper webs, ideally a uniform coating is applied, resulting in uniform gloss over the entire coated surfaces. However, in practice in addition to the coating flaws described above other variations in gloss appear such as caused by variations in formation, flocculation, platelets, etc. Generally, it is only desired to detect linear flaws which require rejection of the coated web while overlooking variations in gloss which are not serious enough to require rejection of the coated web.

The problem with sensing elements that detect variations in gloss is that variations relate not only to linear flaws, but also to most other variations in the paper stock being coated, and in the coating.

It is important therefore to provide a sensing unit which would detect only those flaws which determine whether or not the coating being applied warrants that the coated stock be accepted or rejected. Thus, of the flaws which occur in a coating, rejectable flaws must be distinguished from non-rejectable flaws. Present sensors are not able to accomplish this since they "see" all flaws which results in an unacceptably high rate of rejection. That is, in an automatic inspection system, there is a tendency to report all variations in gloss as flaws.

SUMMARY OF THE INVENTION

In the present invention, a sensing unit is provided which selectively detects flaws on a coated surface, such as a paper web. The flaws to be detected may correspond to a first type of reflected energy from a diffuse surface in contrast to a second type of reflected energy such as from a background specular surface.

Reflected light energy from a coated surface is sensed either above or below or both above and below the theoretical specular angle of reflection. (See Handbook of Pulp and Paper Technology, 2nd Ed., p. 658, for definition of reflective intensities and specular angles.)

When sensing above the spectral angle, the reflection from the coated surface or background will be muted or diminished and the flaw will appear brighter. When sensing below the spectral angle, close to the angle of maximum reflection from the paper, the flaw will appear much darker than the background illumination. In the case of clay-coated stock, the background illumination is reduced also, but to a lesser degree than the flaw. The sensing unit of this invention discriminates among various flaws on a coated surface and provides a signal corresponding to "rejectable" flaws such as linear flaws. Normally, such rejectable flaws are diffuse, while the coated stock surface is specular.

The invention in one aspect provides a sensing unit which detects the reflected energy offset from the theoretical spectral angle. The signal corresponding to the flaw, such as a diffuse reflection from a specular surface is accented with respect to the other reflected variations. The signal corresponding to the flaw is easily distinguished from other background signals.

In another aspect of the invention, the sensing unit receives the reflected energy from either side of the theoretical spectral angle, converts the received reflected energy into signals and combines the signals to generate an output corresponding to the detected flaw.

In a preferred embodiment of the invention, a sensing unit is provided to detect flaws on a surface such as a coated and/or calendared surface.

The sensing unit includes two sensors adapted to receive reflected energy above and below the theoretical spectral angle. The surface per se with myriad small variations in gloss produces signals within a narrow range which signals may be considered noise. The flaw to be detected produces an accented signal when viewed at the proper angles, having a much sharper slope, either negative or positive, which differentiates from the noise. The signals are combined and distinguished from the noise and an output provided indicating a flaw.

DESCRIPTION OF THE PREFERRED EMBODIMENT

The invention will be described in reference to the detection of linear flaws on the coated surface of a moving web, and more particularly to detecting fine scratches on 35-80 gloss magazine stock.

As is well known, paper stock to be coated moves from roll to roll with the coating being applied such as by a doctor blade. To detect flaws which would require rejection of the stock, machines are presently available. The type stock and ultimate use will determine what is acceptable in terms of flaws, such as area flaws, small flaws, linear flaws, etc. Simply, all detection is based on gloss measurement made over the web of the moving coated paper by an array of sensors. The array cans the moving web and imbalances in gloss are sensed and a signal provided. The signal is processed such that an operator may identify the location, frequency, and length of the flaws if desired.

The sensing unit of the present invention may be used with any flaw detection machine, such as a Leigh Control Systems Electronic Machine 131. Accordingly, only the sensing unit will be shown in detail.

Figure 1:
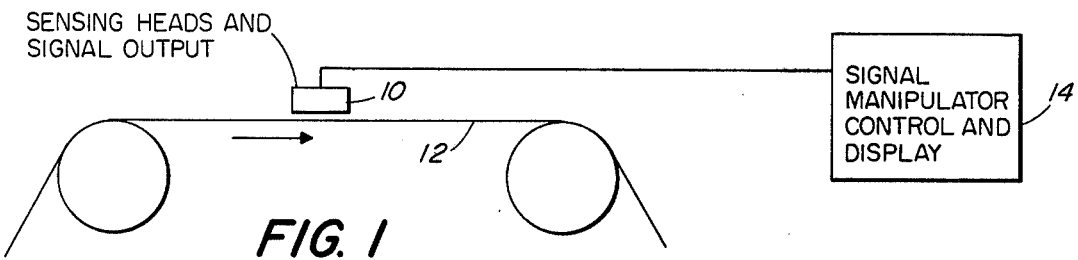
FIG. 1 is a schematic illustration of a sensing head and display unit in combination with a moving web.

As shown in FIG. 1, a sensing head 10 is disposed over a coated web 12 moving at 2000 feet per minute such as magazine stock of between 35-80 gloss. The output from the sensing head is transmitted to a signal manipulation control and display unit 14, which typically provides information as to the length of the flaw, location, etc. Although only one sensing head will be described in detail, it is to be understood that normally a plurality of such sensing heads are arrayed across the web of paper on a suitable support. In this example, the sensing head transverses the web in a reciprocating manner approximately eight inches in one direction.

Figure 2:
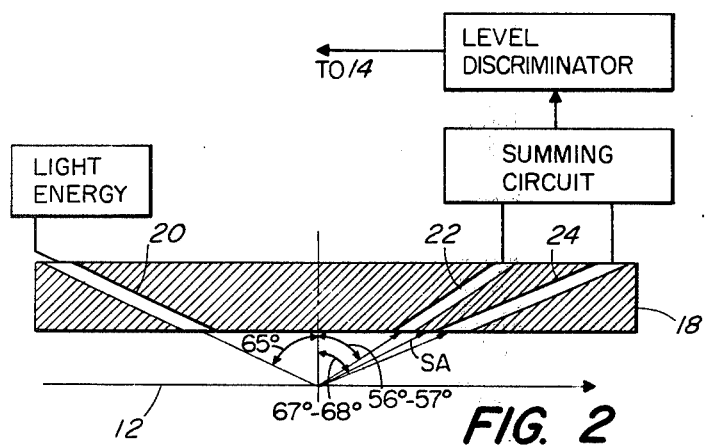
FIG. 2 is a front sectional view of a sensing head used in the preferred embodiment of the invention.

In FIG. 2, a sensing unit is shown in greater detail and comprises a housing 18, a light source 20 such as a CM-20-3 manufactured by Chicago Miniature Lamp Works, Chicago, Ill., and photoresistors 22 and 24 such as CL705H1, manufactured by Clairex Corp., Mount Vernon, N.Y. The light energy from source 20 strikes as an incident beam the coated surface of the web 12 at an intensity of about 700 ft-candles, and is reflected.

This incident beam strikes the coated surface in a direction parallel to the movement of the web 12. The photoresistors 22 and 24 receive the reflected energy at an intensity of about 30 and 200 ft-candles respectively. As shown, the photoresistors 22 and 24 lie in the same plane. The light source 20 and photoresistors 22 and 24 are fixedly secured in the housing 18 at the angles illustrated. As shown, they are moulded in place, but may be secured in any suitable manner. The bottom plane of the housing and the photoresistors are approximately 3/16 inches from the coated surface.

Figure 3:
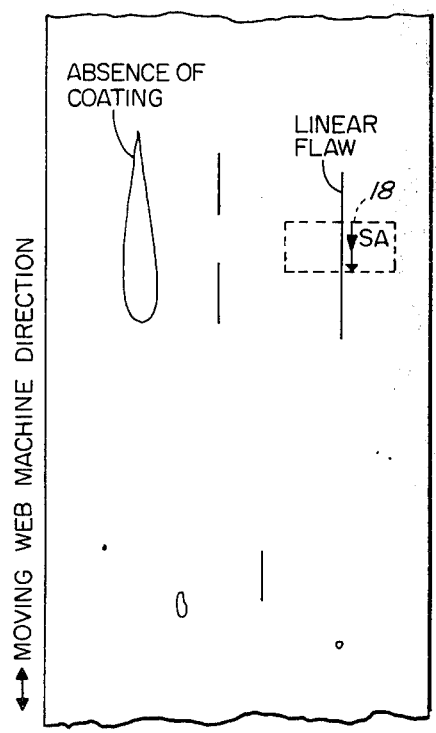
FIG. 3 is a plan view of a coated surface illustrating typical flaws.

Referring to FIG. 3, the sensing unit 18 is shown in dotted lines superimposed over a linear flaw or scratch in the coated surface. The function of the positioning of the photoresistors 22 and 24 is represented graphically in FIG. 4.

Figure 4:
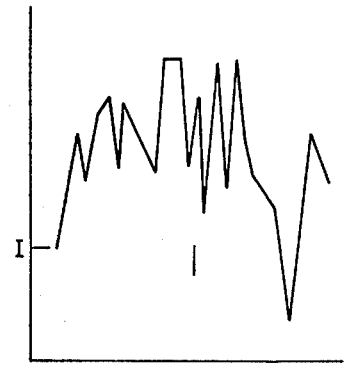
FIGS. 4a, b, c, j and e are graphical representations of the signals being analyzed.
Figure 4:
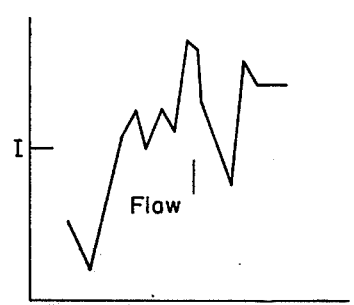
Figure 4:
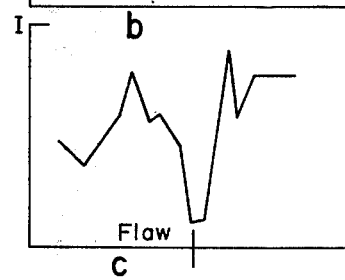
Figure 4:
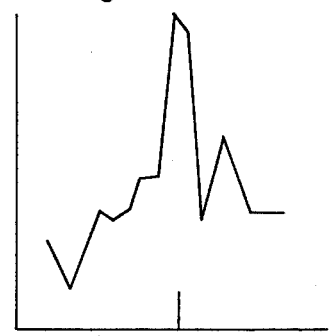

FIG. 4 depicts the various signals corresponding to the coated surface of the web 12 including the linear flaw as shown in FIG. 3. In FIG. 4, the linear flaw of FIG. 3 is viewed at the specular angle. The signal corresponding to the linear flaw viewed at the spectral angle is difficult to distinguish from the other signals corresponding to variations in gloss.

When viewed at the same incident intensity I above the spectral angle at 67°-68°, a bright signal against a generally dark background is provided. In FIG. 4b, the signal corresponding to the linear flaw is more accented.

When viewed at the intensity below intensity below the spectral angle at 56°-57°, a very dark signal against a generally dark background is provided. In FIG. 4c, the signal corresponding to the linear flaw is more accented.

As shown in FIGS. 4b and c, the background signals or noise remain substantially the same while the signal corresponding to the linear flaw changes considerably. In this illustration, the accenting of the signal corresponding to linear flow is essentially because the flaw represents a diffuse reflection from an otherwise specular background. The signals received by the photoresistors 22 annd 24 are algebraically combined electronically to provide a sharply differentiated signal from which is eliminated background noise, and processed as a signal corresponding to a detectable flaw, as shown in FIG. 4d.

Referring to FIG. 2, the signals from the photoresistors 22 annd 24 are at a value of 1.0 to 2.0 volts, depending upon the actual value of the gloss. The signal-to-noise ratio is approximately 2:1 above the spectral angle and 4:1 below the spectral angle. The signals are algebraically summed and amplified in the summing circuit 30 and output in a range of from 2.0 to 8.0 volts. The signal-to-noise ratio is now about 5:1. The lower voltage level will vary and the signal-to-noise ratio will vary such as to 16:1 depending upon how the background noise cancels out. The level discriminator is set at 5 volts where only those signals over 5 volts will be output to signal manipulator and control 14.

In this example, the signal input to be analyzed in the level discriminator has a positive going slope as shown in FIG. 4d. The signals-to-noise (background) ratio is approximately 5:1, and therefore easily handled. Depending upon the surface analyzed, the signal may be a negative going slope or both.

The above invention has been described in reference to detection of linear flaws, which substantially diffuse. It has been particularly designed in reference to magazine stock of a 35-80 gloss and for the detection of fine scratches or linear flaws thereon, the incident angle preverably being 62° and the lower reflected angle being 56°-57°; and the higher reflected angle between about 67°-68°. Another incident angle and corresponding reflected angles that may be used are 70°, 61°-62° and 72°-73° respectively. The specific angles set forth provide the highest signal-to-noise ratio. For the type of stock described in the preferred embodiment, the effect described occurs if the angle of incidense, hereafter referred to as 'i', is limited to angles between 60° and 70°. The corresponding low and high reflecting angles are then defined as i−8° and i+2° respectively. For different paper types and coating types, the range of i may be different, as may be the angular separation of the low and high reflecting angles from the theoretical specular angle.

The invention may also be used to find holidays on a transparent release coating on a cheap grade of stock such as "Sly-Off 23" manufactured by Dow-Corning Corp., Midland, MI. on calendared kraft stock, wherein the incident angle would be approximately 70° and the higher reflected angle 67°-68°, and the lower reflected angle between about 72°-75°. Also, it may be used to detect smudges and scratches on a heavy textured white art paper such as used for sketching, etc. where the incident beam would be approximately 70° and the higher reflected beam would be about 40° and the lower reflected beam about 72°.

Common to all of the above examples is that the flaw being detected and its reflective qualities differentiate substantially from the reflective qualities of the surface per se. In the preferred embodiment, it was described as detecting diffuse flaws from a specular surface. Preferably, the change in surface reflective characteristics would be at least 2:1 on a signal level. However, situations can exist in which the flaw is a relatively specular area on a generally specular background, such as a spot of oil on a coated surface. Contrariwise, the flaw may be a relatively diffuse area on a generally diffuse background, such as a mechanical cut on a matte surface. In cases such as these, the change in surface reflective characteristics between the flaw and the background can yield a ratio barely greater than unity (1:1) when viewed at the theoretical specular angle. In cases such as these, angles of incidence and low and high reflectance may be empirically determined in accordance with the present method to yield a usefully large signal difference.

Further, the sensors of the present invention may be fixedly mounted above a moving web and the sensors adapted for limited oscillatory movement to scan the web. They may be fixed for reciprocating motion across the web and the sensors fixedly secured or a combination thereof.

Although described in reference to detecting the flaws in a coated surface by moving the viewing angle away from the spectral angle, either above or below and combining the signals from both, it is obvious that one may be used either above or below or preferably both to get the greatest signal differentiation.

In the illustrative embodiment, the direction of incident and reflected angles were described as parallel to the direction of the moving web. If a matte surface is scanned, the angles may be transverse to the direction of the moving web. The orientation will depend upon the surface scanned and can be determined simply by positioning the unit to detect the maximum signals received.

Having described my invention, what I now claim is:

1. A sensing unit to detect flaws on a surface wherein there is relative movement between the surface and the sensing unit which comprises:
   (a) means to provide an incident beam of light energy which strikes and is reflected from a portion of the surface, the angle of the incident beam being greater than 45° in reference to a plane normal to the surface;
   (b) at least two sensors, disposed above and below the theoretical specular angle to sense high and low reflected energies from that portion of the surface that intercepts and reflects the incident beam and to provide two types of signals at high and low angles in reference to the theoretical specular angle;
   background signals at the high angle which background signals are diminished with reference to signals corresponding to a flaw and background signals at the low angle, which background signals are accented with reference to signals corresponding to the flaw in said surface;
   (c) means to process the two types of signals corresponding to the energies to distinguish further the signals corresponding to the flaw from the background signals; and
   (d) means to output said distinguished signals.

2. The sensing unit of claim 1, wherein the background signals are noise and the means to process the signal includes means to separate the distinguished signal from the noise when the signal-to-noise ratio is at least 2:1.

3. The sensing unit of claim 2 wherein the means to process includes means to combine the two types of signals.

4. The sensing unit of claim 3 wherein the means to combine includes means to sum the signals.

5. The sensing unit of claim 1, wherein:
   the means to provide an incident beam of light energy includes a light source adapted to strike the surface at an angle, i, of between about 60°–70° and wherein; one sensor is adapted to sense the energy on the low reflecting angle at i−8° and other sensor is adapted to sense the energy on the high reflecting angle at i+2°.

6. The sensing unit of claim 1, wherein:
   the means to provide an incident beam of light energy includes a light source adapted to strike the surface at an angle of about 70°; and wherein;
   one sensor is adapted to sense the energy on the low reflecting angle at about 72° to 75° and the other sensor is adapted to sense the energy on the high reflecting anngle at about 67° to 68°.

7. The sensing unit of claim 1, wherein:
   the means to provide an incident beam of light energy includes a light source adapted to strike the surface at an angle of about 70° and wherein;
   one sensor is adapted to sense the energy on the low reflecting angle at about 40° and the other sensor is adapted to sense the energy on the high reflecting angle at about 72°.

8. The sensing unit of claim 1 wherein the means to process includes;
   means to combine the two types of signals.

9. The sensing unit of claim 8 wherein the means to combine includes means to sum the signals.

10. A method to detect flaws on a surface wherein there is relative movement between the surface and a sensing unit which includes the steps of:
    (a) providing an incident beam of light energy which strikes and is reflected from a portion of the surface, the angle of the incident beam being greater than 45° in reference to a plane normal to the surface;
    (b) sensing the reflected light energy from the portion of the surface struck by the incident beam, at both high and low reflecting angles above and below the theoretical specular angle and to provide two types of signals,
    background signals at the high angle which background signals are diminished with reference to signals corresponding to a flaw in the surface; and
    background signals at the low angle which background signals are accented with reference to signals corresponding to the flaw in said surface;
    (c) processing the background signals and the signal corresponding to the flaw to distinguish further the flaw from the background signals; and
    (d) providing an output corresponding to said distinguished signal.

11. The method of claim 10 which includes combining the signals.

12. The method of claim 11 which includes summing the signals.

13. The method of claim 10 wherein the energy corresponding to the flaw is diffuse and the energy corresponding to the background signals is specular.

14. The method of claim 10 wherein the ratio of the signal corresponding to the flaw to the background signals is at least 2:1.

15. The method of claim 10 which includes:
    providing the incident beam of light energy at an angle i between about 60° to 70°; and
    sensing the reflected light energy above the theoretical specular angle at i+2°; and
    sensing the reflecting energy below the theoretical specular angle at i−8°.

16. The method of claim 15 which includes:
    sensing the light energy at the high reflecting angle at between about 67° to 68°; and
    at the low reflecting angle between about 72° to 75°.

17. The method of claim 16 which includes:
    sensing the low reflected energy at an angle of about 40°; and
    sensing the high reflected energy at an angle at about 72°.

* * * * *